(12) United States Patent
Nourbakhsh

(10) Patent No.: US 12,727,923 B2
(45) Date of Patent: Sep. 8, 2026

(54) EXPANDABLE PEDICLE SCREW ASSEMBLY

(71) Applicant: Ali Nourbakhsh, Atlanta, GA (US)

(72) Inventor: Ali Nourbakhsh, Atlanta, GA (US)

( * ) Notice: Subject to any disclaimer, the term of this patent is extended or adjusted under 35 U.S.C. 154(b) by 0 days.

(21) Appl. No.: 18/391,602

(22) Filed: Dec. 20, 2023

(65) Prior Publication Data

US 2024/0197368 A1 Jun. 20, 2024

Related U.S. Application Data

(60) Provisional application No. 63/476,351, filed on Dec. 20, 2022.

(51) Int. Cl.
*A61B 17/70* (2006.01)
*A61B 17/86* (2006.01)

(52) U.S. Cl.
CPC ...... *A61B 17/7032* (2013.01); *A61B 17/8685* (2013.01); *A61B 2560/0406* (2013.01)

(58) Field of Classification Search
None
See application file for complete search history.

(56) References Cited

U.S. PATENT DOCUMENTS 4,013,071 A * 3/1977 Rosenberg ........... A61B 17/686 411/397
4,917,552 A * 4/1990 Crawford ............. F16B 13/126 411/32
5,716,358 A * 2/1998 Ochoa .................... A61B 17/72 606/301
6,149,669 A * 11/2000 Li ...................... A61B 17/0401 606/68
6,668,688 B2 * 12/2003 Zhao .................. A61B 17/8685 81/439
8,734,497 B2 5/2014 Goel et al.
9,138,219 B2 9/2015 Horrell et al.
11,918,262 B2 * 3/2024 Errico ................ A61B 17/8685
2006/0155281 A1 * 7/2006 Kaup ................... A61B 17/744 606/65
2009/0105771 A1 * 4/2009 Lei ..................... A61B 17/8625 606/301
2009/0281580 A1 * 11/2009 Emannuel .......... A61B 17/8685 606/305

(Continued)

*Primary Examiner* — Jan Christopher L Merene
(74) *Attorney, Agent, or Firm* — BEKIARES ELIEZER LLP

(57) ABSTRACT

Provided herein are various expandable pedicle screw assemblies and associated surgical methods. In one exemplary embodiment, the methods and devices provide a pedicle screw assembly having a support anchor, a retractable shaft or screw, and one or more blades operatively connected to the retractable shaft. Expansion of the retractable shaft within the support anchor may be effective to move the blades between a collapsed configuration and an expanded configuration in which the blades are biased laterally away from the screw assembly. In some embodiments, the biasing of the blades begins along a distal end of the screw assembly and/or the amount of biasing is maximized along the distal end. The retractable shaft may help to impart structural rigidity to the assembly, preventing breakage, while the blades may help to maximize screw purchase with the surrounding bone tissue, preventing displacement and pull-out.

17 Claims, 7 Drawing Sheets

(56) References Cited

U.S. PATENT DOCUMENTS

| | | | | |
|---|---|---|---|---|
| 2010/0185244 | A1 | 7/2010 | Gooch | |
| 2011/0319946 | A1* | 12/2011 | Levy | A61B 17/8685 606/300 |
| 2012/0010668 | A1* | 1/2012 | Shimko | A61B 17/8685 606/313 |
| 2012/0172934 | A1* | 7/2012 | Fisher | A61B 17/8858 606/92 |
| 2019/0125410 | A1* | 5/2019 | Harwell | A61B 17/86 |
| 2020/0100890 | A1 | 4/2020 | Hamilton et al. | |
| 2024/0423685 | A1* | 12/2024 | Oldakowska | A61B 17/742 |

* cited by examiner

EXPANDABLE PEDICLE SCREW ASSEMBLY

RELATED APPLICATION

This application claims the benefit of priority to U.S. application Ser. No. 63/476,351, filed Dec. 20, 2022, which is hereby incorporated in its entirety.

FIELD OF DISCLOSURE

The present disclosure generally relates to pedicle screw assemblies and methods for using the same.

BACKGROUND

A variety of surgical procedures involve implantation of a screw or other fixation device within a bone. When conducted in the spinal column, such procedures are subject to particular difficulties due to the sensitivity of the area and the complexity of the spinal anatomy. Any movement of the screw after implantation may result in injury to the nerve roots or other vital structures as well as resulting in nonunion and pain after surgery.

An additional complicating factor—common in the aging population that typically undergoes such procedures—is osteoporosis. Low bone density may negatively affect the screw purchase, resulting in the screw (and any fixation device attached thereto) becoming loose and even falling out. The result is an increased failure rate of thoracolumbar constructs postoperatively.

Conventional screws designed for implantation in the spine, e.g., in a pedicle, have a threaded shaft that extends through both the cortical bone on the exterior of the pedicle and the cancellous bone within the pedicle and the vertebral body. Because a majority of the screw shaft is located within cancellous bone, which is more likely to suffer bone loss than cortical bone, the result is often poor screw purchase and ultimately implant failure. A recent technology to address the problem is injecting cement inside a cannulated screw. The cement flows through the cannulated shaft and exits via a distal end of the screw and into the bone. However, in addition to the added time and complexity that it adds to the surgical procedure, this technology can result in complications such as cement leakage into the spinal canal and spinal cord vs. nerve injury or extravasation of cement out of the vertebral body and into the vessels, vascular damage, cardiac embolism, pulmonary cement embolism, and anaphylactic shock.

Therefore, there is a need for improved devices and methods for bone screw assemblies, and in particular for bone screw assemblies designed for implantation into the spine.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

In various aspects, the present invention relates to pedicle screws, assemblies and devices and methods for making and using the same. In one aspect, the invention relates to a pedicle screw assembly comprising a bone anchor support with one or more movable blades configured to may expand upon retraction of a shaft, screw, or bolt, or the like to provide increased purchase, gripping or attachment between a shaft, screw, a holding means and/or an bone anchor support, and structural tissue. In another aspect, the invention relates to a pedicle screw assembly comprising a retractable shaft having a distal head portion and a proximal threaded shaft, a cannulated support anchor having one or more movable blades and a threaded channel or inner surface that is configured to mate with the threaded shaft of the retractable shaft In further aspects, the one or more blades may be operatively connected to the retractable shaft. In yet further aspects, the blades may be biased radially outwardly from a collapsed configuration to an expanded configuration upon lateral movement of the retractable shaft within the support anchor. In still further aspects, the pedicles are narrow in the middle and wide as the pedicle attaches to the vertebral body. In some embodiments, an exemplary expandable screw may conform to this "horn" like shape of the pedicle. In yet further aspects, after expansion the screw can take the shape of a "horn" substantially similar to the pedicle since it opens distally and gently and gradually expands proximally. In even further aspects, the pedicle screw assembly can engage the cortical bone of the pedicle and proximal vertebral body and may not be dependent of the cancellous bone as many prior designs are.

In another aspect, the distal head portion of the retractable shaft comprises a spear having a distal point and a proximal abutment edge. The proximal abutment edge of the spear may be configured to push the blades radially outward as the spear travels or moves within the support anchor. In further aspects, this configuration can also support the blades and decrease the risk of future collapse of the blades.

In another aspect, at least one of the one or more blades has a sloped inner surface terminating in a sharp point along a distal end thereof, the sloped inner surface being configured to abut the proximal abutment edge of the spear as the spear slides within the support anchor.

In some embodiments, biasing of the blades begins along a distal portion of the screw assembly upon retraction of the retractable shaft within the support anchor. The blades may be biased to varying degrees along an entire length of the screw assembly in the expanded configuration.

In some embodiments, the one or more blades comprises two blades disposed on opposing outer surfaces of the support anchor. In other embodiments, the one or more blades comprises four blades, each of the four blades being disposed opposite to another along an outer surface of the support anchor. At least one of the one or more blades may have a plurality of pointed projections extending radially therefrom.

In some embodiments, the screw assembly is substantially cylindrical when in the contracted configuration.

In another embodiment, the pedicle screw assembly can comprise a retractable shaft having a distal head portion and a proximal threaded shaft, a cannulated support anchor having a proximal, threaded inner surface that is configured to mate with the threaded shaft of the retractable shaft and a distal, open cavity for housing the distal head portion of the retractable shaft therein, and one or more blades operatively connected to the distal head portion of the retractable shaft. The blades expand radially outwardly through slots, grooves, or apertures in the support anchor upon lateral movement of the retractable shaft within the support anchor.

In some embodiments, the one or more blades comprise two blades disposed on opposing outer surfaces of the support anchor. In other embodiments, the one or more blades comprise four blades, each of the four blades being disposed opposite to another along an outer surface of the support anchor.

One embodiment of a method of implanting a screw assembly inside a patient may comprise forming a channel in a patient's spine; inserting the screw assembly into the channel in a collapsed configuration, the screw assembly comprising a retractable shaft, a cannulated support anchor with one or more blades; and proximally retracting the retractable shaft within the support anchor to bias one or more blades into an expanded configuration in which the one or more blades extend axially away from the screw assembly.

In some embodiments, retracting the screw comprises rotating the screw within the support anchor, such that threads of the screw engage inner threads of the support anchor. In some embodiments, the biasing of the blades begins along a distal portion of the screw assembly. The biasing of the blades may involve biasing the blades along an entire longitudinal length of the screw assembly.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

Figure 1:
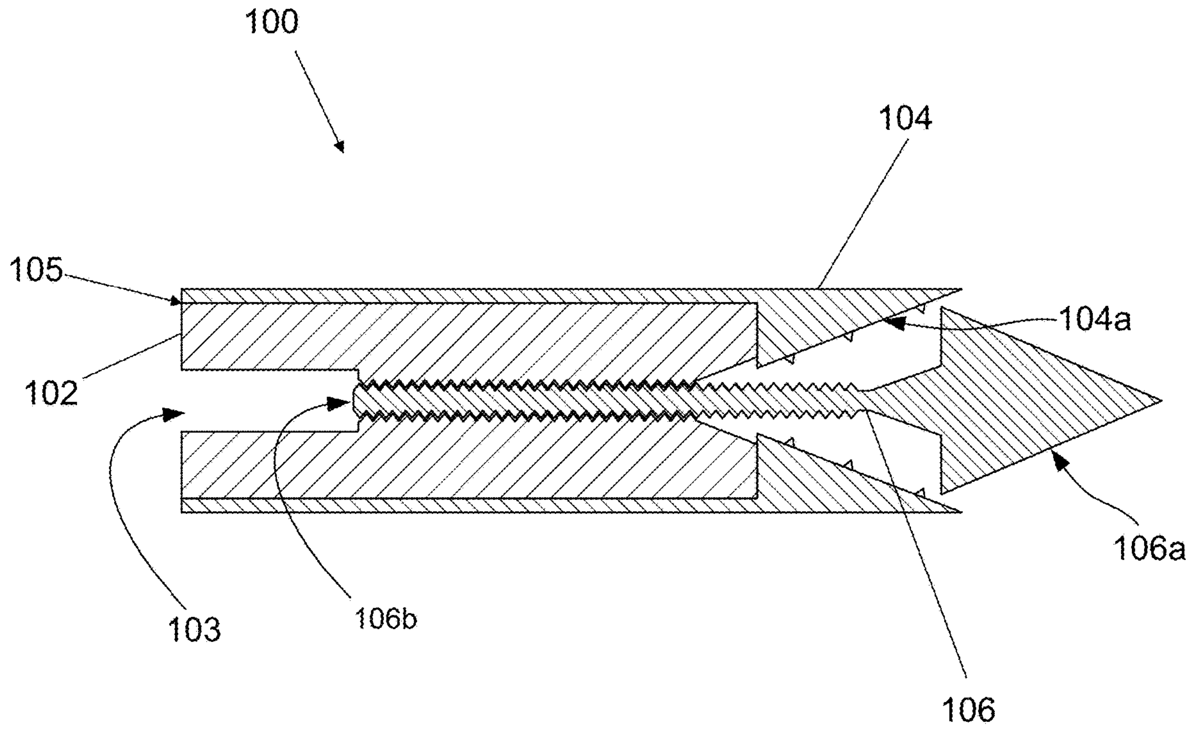
FIG. 1 is a side, cross-sectional view of an example embodiment of a pedicle screw assembly in the collapsed configuration in accordance with the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, “a” and “an” each generally denotes “at least one,” but does not exclude a plurality unless the contextual use dictates otherwise. When used herein to join a list of items, “or” denotes “at least one of the items,” but does not exclude a plurality of items of the list. Finally, when used herein to join a list of items, “and” denotes “all of the items of the list.”

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of pedicle screws and associated procedures, embodiments of the present disclosure are not limited to use only in this context. It will be appreciated that screw assemblies according to the present disclosure may be suitable for use in any medical procedure that involves implantation of a screw, anchor, bolt, or other fixation device within a bone. In particular, screw assemblies according to the present disclosure may be useful in medical procedures that require long-term, stable implantation within a patient.

Embodiments of the present disclosure include expandable pedicle screw assemblies having one or more moveable portions or blades configured to be biased axially away from the screw assembly and into bone tissue, to help secure the screw assembly within the bone. In various further embodiments, the pedicle screw assembly may comprise a support anchor with movable portions and an expansion mechanism, such as a shaft, screw or bolt, configured for insertion and/or retraction into the support anchor. The support anchor (which may also be referred to as a ‘cannulated support anchor’, ‘bone anchor’, ‘bone anchor support’ or ‘anchoring support’) may comprise or otherwise be constructed to have one or more movable portions such as external wall blades or members that may expand or move outwards upon lateral movement of the expansion mechanism (e.g., a shaft, a screw, a bolt, or the like) to provide increased gripping or attachment between a screw, a blade, gripping means, a holding means and/or support anchor, and structural tissue.

In further aspects, the support anchor may have one or more grooves or slits along its wall(s) that enable various parts of the support anchor or wall members to expand upon retraction of a screw or bolt, or the like. In still further aspects, either or both the inner and outer surfaces and/or walls of the support anchor(s) may be tapered, straight, threaded, and/or smooth. An opening in the support anchor for lateral movement of expansion mechanisms (e.g., screw, bolt, etc.) may be of varying dimensions to accommodate a desired diameter or length of screw. A screw, bolt, or the like, may be pre-inserted into, attached or affixed to the support anchor so as to expand the moveable portion, wall members or blades on the support anchor upon retraction of the expansion mechanism. The external surface size of the support anchor with an expansion mechanism such as a retractable screw or bolt inserted therein may increase gripping or attachment between the structural tissue (e.g., bone) and the support. In various embodiments, the support anchor may provide for reduction of motion of a pedicle or bone screw, that may be caused by the movement of the instrumentation or bone, so as to reduce friction and/or structural tissue wear-out, for example, by including a moveable portion or outwardly biasing blades to the support anchor.

In some embodiments, the pedicle screw assembly may comprise a cannulated support anchor, a retractable shaft configured for insertion into the support anchor, and one or more blades. While the term “blades” is used herein to describe the expanding or biasing members of the illustrated embodiments, it will be appreciated that screw assemblies as provided herein may include any biasing member suitable for assisting with bone purchase, e.g., fins, tabs, projections, and the like.

The blades may be operatively connected to the retractable shaft, such that lateral movement of the retractive shaft may be effective to move the screw assembly between a collapsed configuration, where the blades are retracted, and an expanded configuration, where the blades are biased axially away from the screw assembly or support anchor. The presence of the outer shaft portion may help ensure structural rigidity of the screw assembly in the expanded configuration, while the blades expand into the vertebral body cancellous bone to prevent the screw assembly from moving or pulling out. In further aspects, the distal end of the blades will rest and be supported by the retractable shaft. In some embodiments, the pedicle screw assembly may comprise a plurality of blades, for example, 2, 3, 4, 5, 6, 7, 8, 9, 10 or more blades. In other embodiments, the blades are biased axially away from the screw assembly to varying amounts, e.g., the biasing may be greater along a distal portion of the screw assembly then along a proximal portion. Furthermore, the number of blades, degree of biasing, and/or location of the blades may be configured to ensure maximum purchase for a particular anatomy. In still further aspects, each of the plurality of blades may be configured to selectively bias or expand from the screw assembly. For example, in some embodiments, one or more of the blades may be configured not to bias or expand. In other embodiments, one or more of the blades may be configured to bias or expand less than other blades and/or a delayed bias or expansion. In yet further aspects, the blades may be configured to selectively bias or expand laterally and/or superiorly but not inferiorly and/or medially, for example and without limitation, if the screw assembly was put in more towards the medial and inferior wall of the pedicle and due to weak bone, the surgeon does not want to violate the pedicle wall.

In further aspects, dimensions of the screw assembly may vary depending on the anatomy and position in which it will be implanted. For example, a length of the pedicle screw may be in a range of about 10 mm to 50 mm, for example about 25-30 mm. For example, a length of the retractable shaft may be in a range of about 10 mm to 35 mm, for example about 25-30 mm. A length of the one or more blades may be in a range of about 30 to 60 mm. Where the blade is spear-shaped, a length of the head of the spear may be in a range of about 5 to 25 mm and a length of the shaft of the spear may be in a range of about 15 to 35 mm. A diameter of the screw assembly in the expanded configuration may be in a range of about 2 to 10 mm. A diameter of the screw assembly in the collapsed configuration may be in a range of about 1 to 8 mm.

It will be appreciated that any of the screw assembly components described herein may have one or more surface features to assist with implantation, bone purchase, and/or osteointegration. For example, any of the components described herein may have a textured or roughened outer surface that may be, for example, threads, cylindrical ribs, nubs or bumps, and the like. Similarly, any of the screw assembly components described herein may be composed of one or more materials to assist with implantation, bone purchase, biocompatibility, and/or osteointegration. By way of non-limiting example, the screw assembly may comprise bio-compatible material(s), for example, allograft, allograft bone; polyetheretherketones (PEEK), high molecular weight polyethylene (HMWPE), carbon fiber, and/or any other synthetic material that can be manufactured and implanted into the body, etc. Some components, e.g., the screw and the blades, may be comprised of a metal, which may be flexible. It will be appreciated that each of the components may be composed of the same or different materials.

Screw Assembly and System Configuration

According to various aspects of the invention, the screw assemblies, devices and systems of the present disclosure can comprise multiple configurations. FIGS. 1-7 illustrate non-limiting examples of embodiments of operating environments, mechanisms, and components for the disclosed assemblies, devices, and systems. Although the operating environments, mechanisms, and components are disclosed with specific functionality, it should be understood that functionality may be shared between mechanisms and/or components, with some functions split between mechanisms and/or components, while other functions duplicated by the mechanisms and/or components. Furthermore, the name of the mechanisms and/or components should not be construed as limiting upon the functionality of the mechanisms and/or components. Moreover, each stage in the claim language can be considered independently without the context of the other stages. Each stage may contain language defined in other portions of this specifications. Each stage disclosed for one mechanism and/or component may be mixed with the operational stages of another mechanism and/or component. Each stage can be claimed on its own and/or interchangeably with other stages of other mechanisms and/or components.

Figure 2:
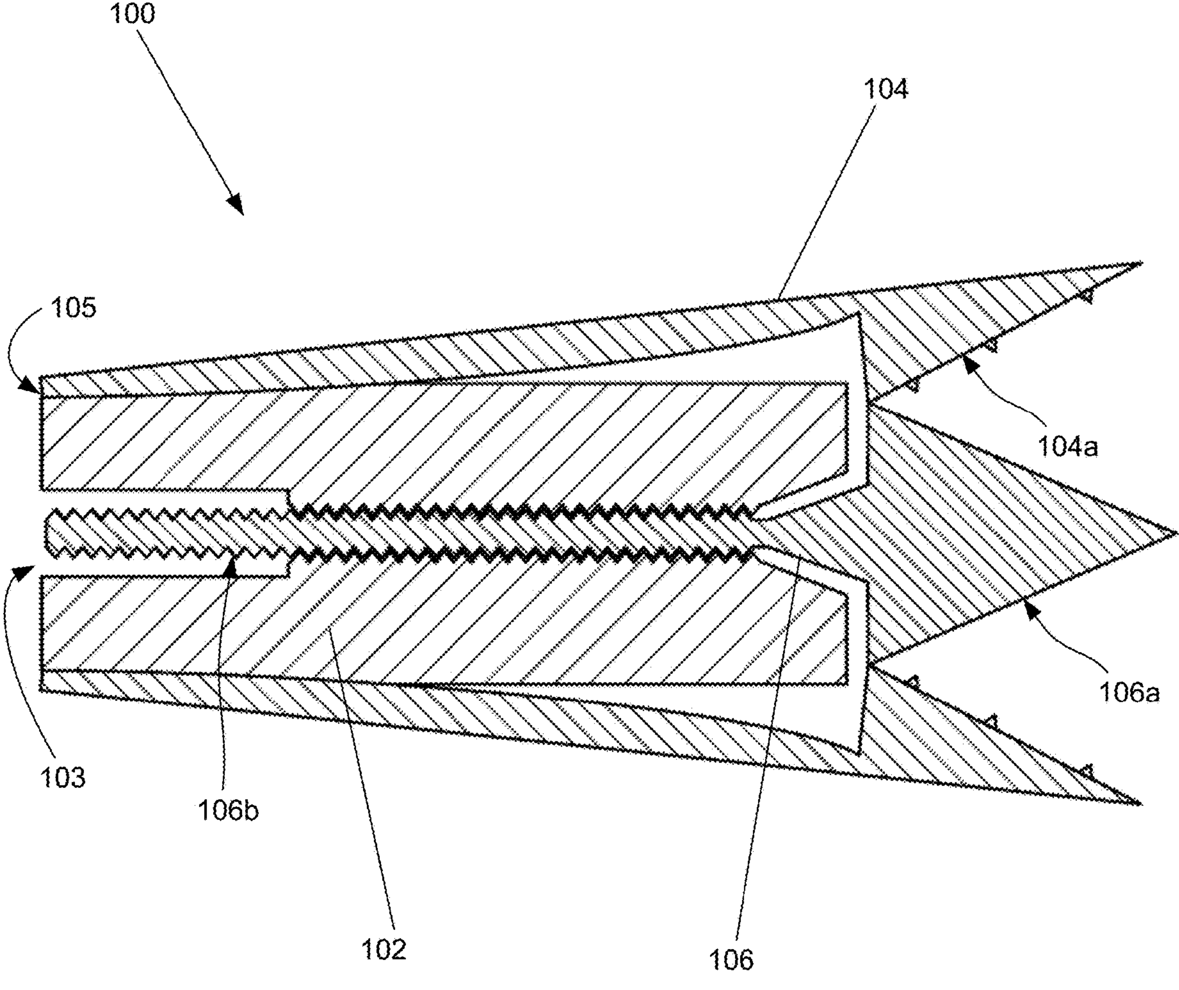
FIG. 2 is a side, cross-sectional view of the pedicle screw assembly of FIG. 1 in the expanded configuration in accordance with the present disclosure.
Figure 3:
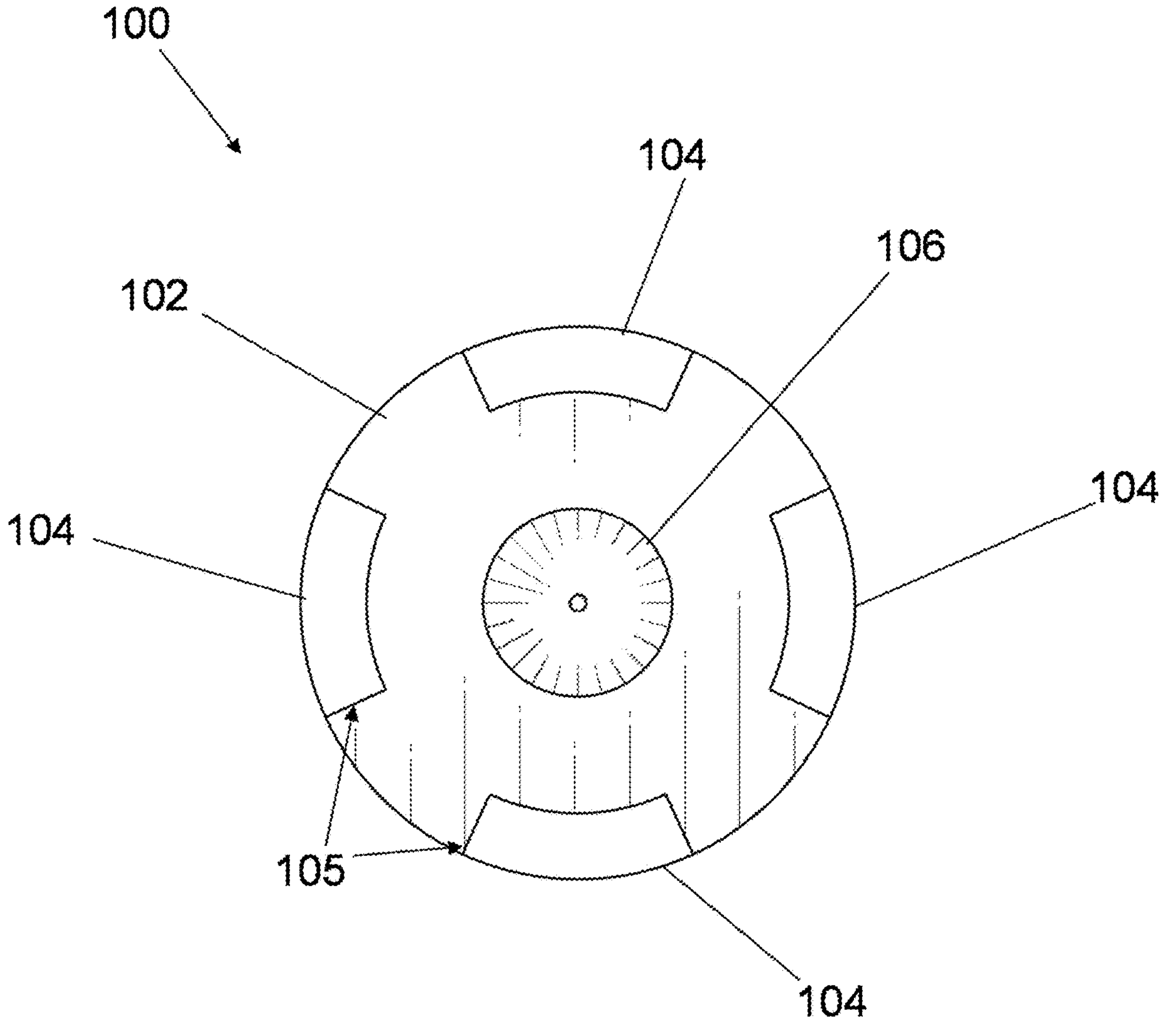
FIG. 3 is a top cross section view the pedicle screw assembly of FIG. 1 in accordance with the present disclosure.

By way of non-limiting example, FIGS. 1-3 show various views a pedicle screw assembly 100 in accordance with an example embodiment of the present invention. FIG. 1 illustrates pedicle screw assembly 100 in a collapsed configuration. The pedicle screw assembly 100 may comprise a cannulated support anchor 102 with four movable elongate blades 104 disposed in slots or grooves 105 along an outer surface of the support anchor, and a retractable shaft 106 having a distal head portion **106*a* and a proximal threaded shaft body 106*b***. The retractable shaft (which may also be referred to herein as a "retractable pedicle screw", "retractable screw", or "retractable pedicle screw shaft") may movably engage with the support anchor via the mating of threads on the outer surface of the screw with threads on the inner surface of the support anchor. The movable blades may be fixedly connected to the support anchor along at least some portion of the one or more blades. In the illustrated embodiment, the blades are fixedly connected to the support anchor along a proximal end of the blades but are capable of axial movement away from the support anchor when moving between the collapsed and expanded configurations.

The one or more blades may have any form suitable for enhancing bone purchase of the screw assembly. In the illustrated embodiment, the blades have an elongated shape with a proximal shaft portion and a distal spear portion. The distal spear portion may comprise a sloped surface terminating in a sharp tip at the distal-most end, which may facilitate inserting the screw assembly into the bone and/or preventing movement of the screw assembly with respect to the bone after implantation. In some embodiments, to facilitate biasing of the blades away from the screw assembly, the blades may be made of a flexible material such as titanium and the like.

In various aspects, an external surface of the blades may be smooth, comprise threads or at least one surface treatment, and/or may have some kind of texture configured to improve purchase of the assembly with the surrounding bone tissue. For example, in some embodiments, the external surface of the blades may be textured, may have a plurality of teeth thereon, may have threads extending therearound, and the like. As illustrated in the embodiment of FIGS. 1-3, external surface **104*a* of the blades may have a plurality of pointed projections extending radially therefrom. In other embodiments, external surface 104*a* of the blades may have continuous threads configured to cooperate with retractable shaft 106** during use, to allow for easier travel (i.e. insertion and retraction).

As described herein, the number of blades, degree of biasing, and/or location of the blades may be configured to ensure maximum purchase for a particular anatomy. A number of blades provided in the screw assembly may vary depending on the anatomy in which the assembly is to be implanted. For example, in sites having space constraints, the screw assembly may only include two blades. Where there is more space and/or additional need for bone purchase, the screw assembly may have four or more blades. Similarly, a location of the blades may vary to ensure optimal bone purchase in a particular bone anatomy. In the illustrated embodiment, the blades are spaced apart at regular intervals around a circumference of the support anchor, with each blade being opposite to another blade. Depending on the screw position and surgeon preference different screw embodiments can be used.

To this end, in other embodiments, the pedicle screw assembly may comprise a plurality of blades, for example, 2, 3, 4, 5, 6, 7, 8, 9, 10 or more blades. In further aspects, the blades may be configured to expand or bias axially away from the screw assembly to varying amounts, e.g., the biasing may be greater along a distal portion of the screw assembly then along a proximal portion. In still further aspects, each of the plurality of blades may be configured to selectively bias or expand from the screw assembly. For example, in some embodiments, one or more of the blades may be configured not to bias or expand. In other embodiments, one or more of the blades may be configured to bias or expand less than other blades and/or a delayed bias or expansion. In yet further aspects, the blades may be configured to selectively bias or expand laterally and/or superiorly but not inferiorly and/or medially, for example and without limitation, if the screw assembly was put in more towards the medial and inferior wall of the pedicle and due to weak bone, the surgeon does not want to violate the pedicle wall. In yet further embodiments, one or two or more of the blades are not expandable. In further aspects, the non-expanding blades may not be thinner or thicker proximally and/or distally, and the thickness may be the same throughout the entire length of the blade.

The retractable shaft may be configured to operatively engage one or more of the blades, to move the blades between the expanded and collapsed configurations. In the illustrated embodiment, the screw comprises a proximal shaft body portion and a distal head portion. The proximal shaft portion may have external threads along at least a partial length thereof. The external threads may be configured to mate with internal threads of the support anchor, thus enabling lateral movement of the screw within the support anchor upon relative rotation of the screw with respect to the support anchor. In further aspects, each of the blades may be configured to selectively engage with the retractable shaft at various positions along the travel path of the retractable shaft. For example, a first blade or first pair of blades may be configured to engage with the retractable shaft and begin to expand at first position along the travel path of the retractable shaft, and a second blade or second pair of blades may be configured to engage with the retractable shaft and begin to expand at a second position farther down (i.e., more proximal) the travel path of the retractable shaft. To this end, the surgeon may be able to decide how many blades to deploy or expand based on how far the retractable shaft is retracted. If the surgeon decides that the bone surrounding pedicle walls are too weak, then only the first blade or pair of blades can be selectively deployed or expanded.

The head portion of the screw may help facilitate insertion and/or bone purchase upon implantation. By way of non-limiting example, the head portion may be spear-shaped, with a distal end of the spear terminating in a sharp point. When assembled together with the other components of the screw assembly, the sharp point of the retractable shaft may be configured to extend distally beyond the support anchor and/or the one or more blades. In this way, the sharp head of the screw may assist with implantation and/or screw purchase.

Additionally, or alternatively, the head portion of the screw may be configured to operatively engage one or more of the blades, to bias them outwardly into the expanded configuration. In the illustrated embodiment, a proximal-facing surface of the screw head defines an abutment surface and/or an abutment edge. When assembled together with the other components of the screw assembly, the abutment edge may be configured to contact an inner-facing surface of the blades, to help bias them away from the support anchor. The further the screw moves in a proximal direction, the further the blades are biased away from the support anchor.

The support anchor may help to assist with structural stability of the screw assembly, particularly when in the expanded configuration. In the illustrated embodiment, the support anchor comprises a cannula, through which the retractable shaft may be inserted. To facilitate stable positioning of the screw within the support anchor, at least a portion of the inner surface of the cannula may have threads that are configured to mate with the screw threads. However, it will be appreciated that a variety of mating mechanisms may allow for the desired lateral movement of the screw during placement with respect to the support anchor and for stable fixation once a desired placement is reached.

In some embodiments, an inner diameter of the cannula may be sufficiently large to accommodate a retractable shaft and/or tools for manipulating the screw therein. By way of non-limiting example, the inner diameter of the cannula may be in a range of about 0.5-5 mm. It will be appreciated that an inner diameter of the cannula may vary from the proximal to the distal ends. For example, in the illustrated embodiment, a proximal portion of the cannula has a larger inner diameter than a distal portion, e.g., such that the proximal portion can accommodate a screwdriver or other tool therein while the distal portion may securely mate with the screw. An outer diameter of the cannula may be sufficiently larger than the inner diameter to ensure a thickness that can impart structural stability, e.g., in a range of about 1-8 mm. The support anchor may be composed of a material sufficiently rigid to maintain the structural stability of the screw assembly.

In further aspects, the screw assembly components can be made of nonabsorbable or bioresorbable material, including biocompatible metals, plastic, ceramics, and composites thereof. In some embodiments, the components can be made of titanium, nitinol, stainless steel, polylactic acid (PLA, PLLA, or PLDLA), polyglycolic acid (PGA), polyether ether ketone (PEEK), or polyacetal. Other types of materials may be utilized in accordance with the invention, and the above are presented only as examples. In still further aspects, the screw assembly components can be made to include or be coated with a biocompatible material, for example, allograft, allograft bone, polyetheretherketones (PEEK), high molecular weight polyethylene (HMWPE), carbon fiber, and/or any other synthetic material that can be manufactured and implanted into the body, etc. In some embodiments, the support anchor may be coated with, for example, hydroxylapatite, bone morphogenetic protein, or other such materials, etc., that may promote or induce the formation of structural tissue including, for example, bone, cartilage, etc. In other embodiments, the walls of the support anchor and/or blades may be threaded, ribbed, studded, or otherwise textured to allow the support anchor to be more securely or easily placed and to increase attachment strength (purchase) between the structural tissue and support anchor.

In general, the collapsed configuration of the pedicle screw assembly may be designed to facilitate insertion of the screw assembly into a predefined cavity within a patient's bone. Relative to the expanded configuration, the collapsed configuration of the screw assembly may have a lower profile, e.g., a smaller outer diameter. For example, in the collapsed configuration, the assembly may be substantially cylindrically shaped, with each of the blades extending parallel to and in close contact with an outer surface of the support anchor. However, it will be appreciated that the assembly may generally be the same shape as a bore or cavity into which it is to be implanted.

FIG. 2 illustrates the pedicle screw assembly 100 in the expanded configuration. In this configuration, the one or more blades 104 are attached, welded, or otherwise coupled at the base such that they are configured to bias axially away from a longitudinal axis of the retractable screw 106 and/or the cannulated support anchor 102. In some embodiments, the screw assembly 100 is configured to transition between the collapsed (FIG. 1) and expanded (FIG. 2) configurations upon movement of the retractable screw 106 or a similarly structured shaft within cannula or channel 103 of support anchor 102, e.g., by retracting the retractable screw 106 within cannula 103. In particular, the proximal-facing abutment surface and/or abutment edge of the screw head **106*a* may contact the inner-facing surface 104*a* of one or more of the blades. For example, as the screw is retracted within the support anchor, the abutment surface of the retractable shaft head may slide along the threaded inner surface 104*a* of the blades 104**, thus pushing the blades outwardly until the screw assembly reaches a desired outer diameter.

Figure 4:
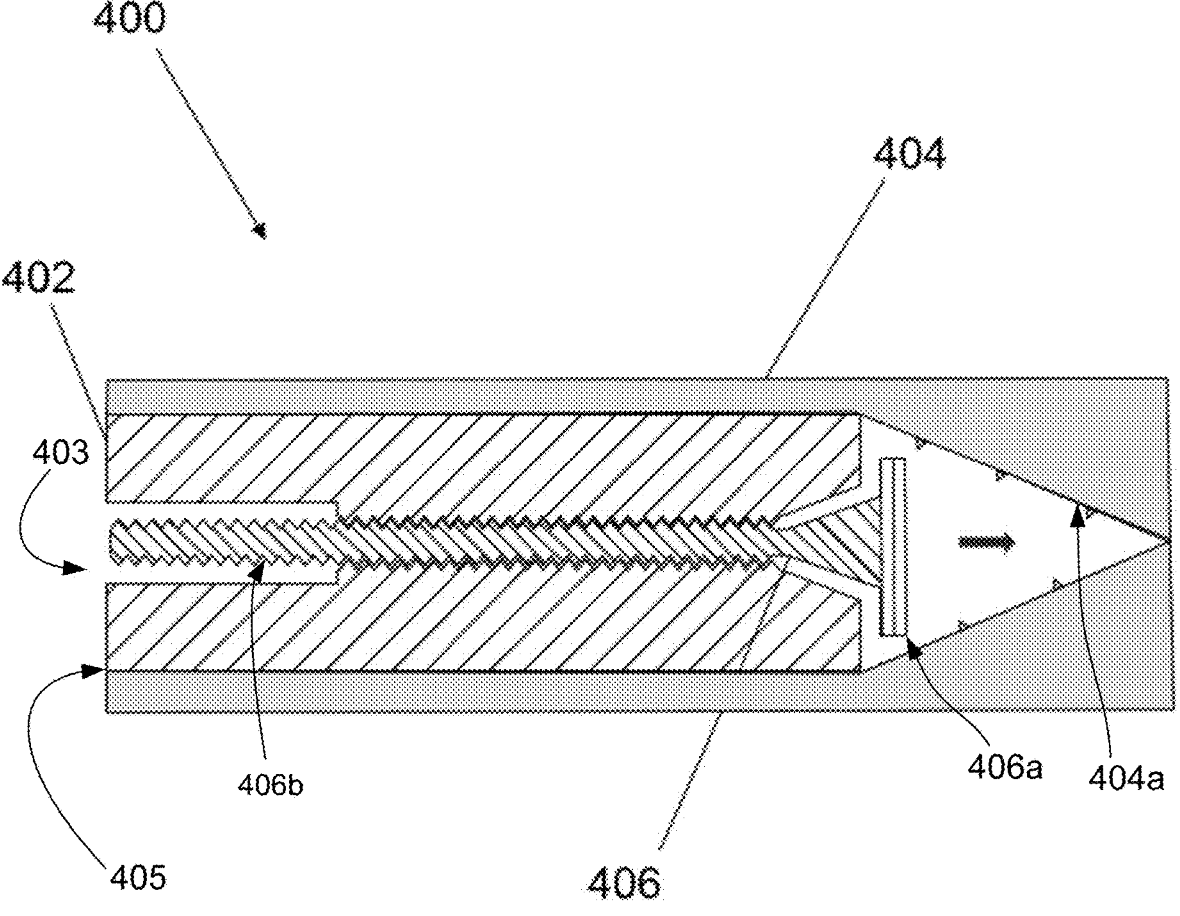
FIG. 4 is a side, cross-sectional view of an example embodiment of a pedicle screw assembly in the collapsed configuration in accordance with the present disclosure.
Figure 5:
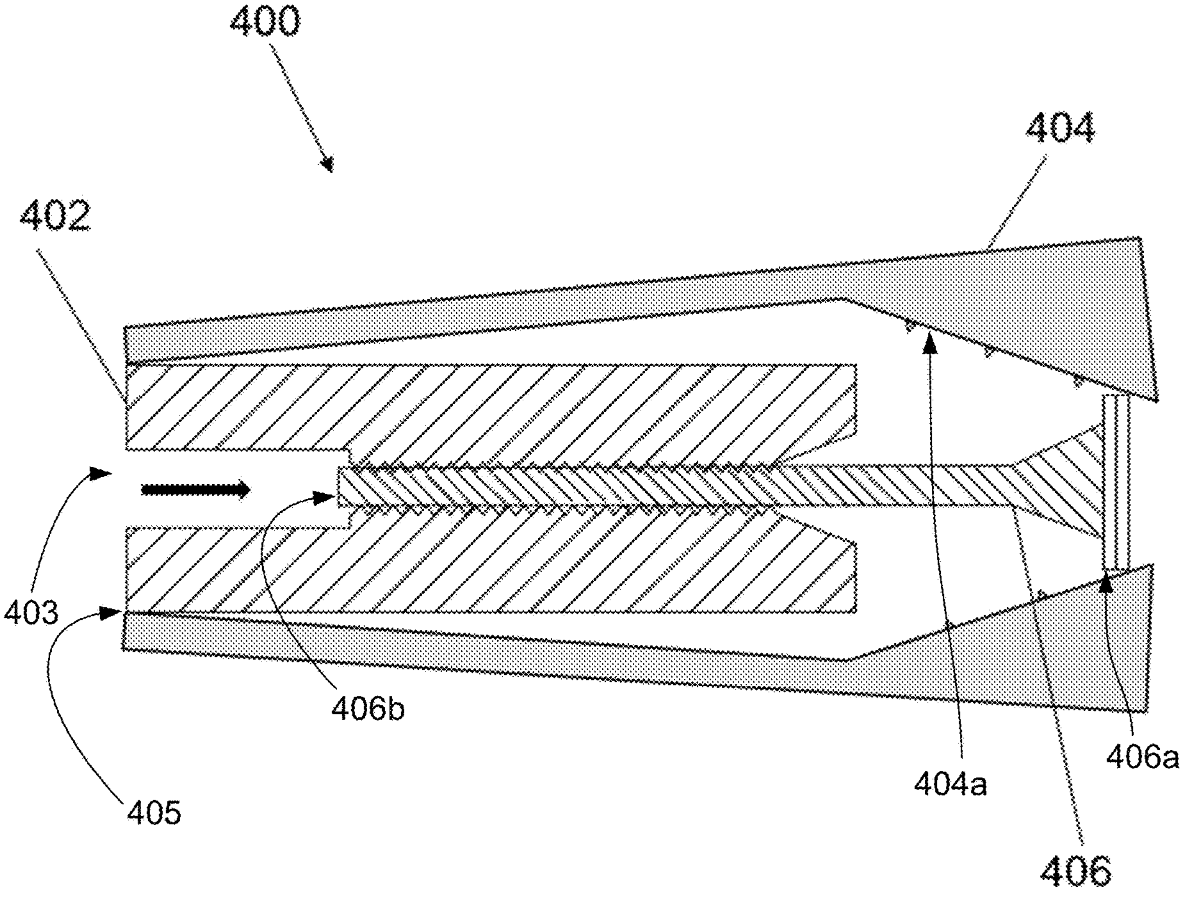
FIG. 5 is a side, cross-sectional view of the pedicle screw assembly of FIG. 4 in the expanded configuration in accordance with the present disclosure.

FIGS. 4-5 show various views a pedicle screw assembly 400 in accordance with another example embodiment of the present invention. FIG. 1 illustrates pedicle screw assembly 400 in a collapsed configuration. The pedicle screw assembly 400 may comprise a cannulated support anchor 402 with a plurality of movable elongate blades 404 disposed in slots or grooves 405 along an outer surface of the support anchor, and a retractable shaft 406 having a distal head portion 406*a* and a proximal threaded shaft body 406*b*. In further aspects, the retractable shaft (which may also be referred to herein as a "retractable pedicle screw", "retractable screw", or "retractable pedicle screw shaft") may laterally movably engage with the support anchor via the mating of threads on the outer surface of the screw with threads on the inner surface of the support anchor. The movable blades may be fixedly connected to the support anchor along at least some portion of the one or more blades. In the illustrated embodiment, the blades are fixedly connected to the support anchor along a proximal end of the blades but are capable of axial movement away from the support anchor when moving between the collapsed and expanded configurations.

The plurality of blades may have any form suitable for enhancing bone purchase of the screw assembly. In the illustrated embodiment, the blades have an elongated shape with a proximal shaft portion and a distal reverse spear head portion. The distal reverse spear head portion may be thickest at the most distal portion of the head portion and comprise a sloped surface terminating at the start of the proximal shaft portion. In some embodiments, to facilitate biasing or curving of the blades away from the screw assembly, the blades may be made of a flexible material such as titanium and the like.

In various aspects, an external surface of the blades may be smooth, comprise threads or at least one surface treatment, and/or may have some kind of texture configured to improve purchase of the assembly with the surrounding bone tissue. For example, in some embodiments, the external surface of the blades may be textured, may have a plurality of teeth thereon, may have threads extending therearound, and the like. As illustrated in FIGS. 4-5, external surface 404*a* of the blades may have a plurality of pointed projections extending radially therefrom. In other embodiments, external surface 404*a* of the blades may also have continuous threads configured to cooperate with retractable shaft 406 during use, to allow for easier travel (i.e., insertion and retraction).

As described herein, the number of blades, degree of biasing, and/or location of the blades may be configured to ensure maximum purchase for a particular anatomy. A number of blades provided in the screw assembly may vary depending on the anatomy in which the assembly is to be implanted. For example, in sites having space constraints, the screw assembly may only include two blades. Where there is more space and/or additional need for bone purchase, the screw assembly may have four or more blades. Similarly, a location of the blades may vary to ensure optimal bone purchase in a particular bone anatomy. In the illustrated embodiment, the blades are spaced apart at regular intervals around a circumference of the support anchor, with each blade being opposite to another blade. Depending on the screw position and surgeon preference different screw embodiments can be used. To this end, in other configurations, the pedicle screw assembly may comprise a plurality of blades, for example, 2, 3, 4, 5, 6, 7, 8, 9, 10 or more blades. In further aspects, the blades may be configured to expand or bias axially away from the screw assembly to varying amounts, e.g., the biasing may be greater along a distal portion of the screw assembly than along a proximal portion. In still further aspects, each of the plurality of blades may be configured to selectively bias or expand from the screw assembly. For example, in some embodiments, one or more of the blades may be configured not to bias or expand. In other embodiments, one or more of the blades may be configured to bias or expand less than other blades and/or a delayed bias or expansion. In yet further aspects, the blades may be configured to selectively bias or expand laterally and/or superiorly but not inferiorly and/or medially, for example and without limitation, if the screw assembly was put in more towards the medial and inferior wall of the pedicle and due to weak bone, the surgeon does not want to violate the pedicle wall. In yet further embodiments, one or two or more of the blades are not expandable. In further aspects, the non-expanding blades may not be thinner or thicker proximally and/or distally, and the thickness may be the same throughout the entire length of the blade.

The retractable shaft may be configured to operatively engage one or more of the blades, to move the blades between the expanded and collapsed configurations. In the illustrated embodiment, the screw comprises a proximal shaft body portion and is configured to travel from proximal to distal in order to expand. The proximal shaft body portion may have external threads along at least a partial length thereof. The external threads may be configured to mate with internal threads of the support anchor, thus enabling lateral movement of the screw within the support anchor upon relative rotation of the screw with respect to the support anchor.

The head portion of the screw may help facilitate insertion and/or bone purchase upon implantation. By way of non-limiting example, the head portion may be spear-shaped, with a distal end of the spear terminating in a sharp point. When assembled together with the other components of the screw assembly, the sharp point of the retractable shaft may be configured to extend distally beyond the support anchor and/or the one or more blades. In this way, the sharp head of the screw may assist with implantation and/or screw purchase.

Additionally or alternatively, the head portion of the screw may be configured to operatively engage one or more of the blades, to bias them outwardly into the expanded configuration. In the illustrated embodiment, a proximal-facing surface of the screw head defines an abutment surface and/or an abutment edge. When assembled together with the other components of the screw assembly, the abutment edge may be configured to contact an inner-facing surface of the blades, to help bias them away from the support anchor. The further the screw moves in a proximal direction, the further the blades are biased away from the support anchor.

The support anchor may help to assist with structural stability of the screw assembly, particularly when in the expanded configuration. In the illustrated embodiment, the support anchor comprises a cannula, through which the retractable shaft may be inserted. To facilitate stable positioning of the screw within the support anchor, at least a portion of the inner surface of the cannula may have threads that are configured to mate with the screw threads. However, it will be appreciated that a variety of mating mechanisms may allow for the desired lateral movement of the screw during placement with respect to the support anchor and for stable fixation once a desired placement is reached.

In some embodiments, an inner diameter of the cannula may be sufficiently large to accommodate a retractable shaft and/or tools for manipulating the screw therein. By way of non-limiting example, the inner diameter of the cannula may be in a range of about 0.5-5 mm. It will be appreciated that an inner diameter of the cannula may vary from the proximal to the distal ends. For example, in the illustrated embodiment, a proximal portion of the cannula has a larger inner diameter than a distal portion, e.g., such that the proximal portion can accommodate a screwdriver or other tool therein while the distal portion may securely mate with the screw. An outer diameter of the cannula may be sufficiently larger than the inner diameter to ensure a thickness that can impart structural stability, e.g., in a range of about 1-8 mm. The support anchor may be composed of a material sufficiently rigid to maintain the structural stability of the screw assembly.

In further aspects, the screw assembly components can be made of nonabsorbable or bioresorbable material, including biocompatible metals, plastic, ceramics, and composites thereof. In some embodiments, the components can be made of titanium, nitinol, stainless steel, polylactic acid (PLA, PLLA, or PLDLA), polyglycolic acid (PGA), polyether ether ketone (PEEK), or polyacetal. Other types of materials may be utilized in accordance with the invention, and the above are presented only as examples. In still further aspects, the screw assembly components can be made to include or be coated with a biocompatible material, for example, allograft, allograft bone, polyetheretherketones (PEEK), high molecular weight polyethylene (HMWPE), carbon fiber, and/or any other synthetic material that can be manufactured and implanted into the body etc. In some embodiments, the support anchor may be coated with, for example, hydroxylapatite, bone morphogenetic protein, or other such materials, etc., that may promote or induce the formation of structural tissue including, for example, bone, cartilage, etc. In other embodiments, the walls of the support anchor and/or blades may be threaded, ribbed, studded, or otherwise textured to allow the support anchor to be more securely or easily placed and to increase attachment strength (purchase) between the structural tissue and support anchor.

In general, the collapsed configuration of the pedicle screw assembly may be designed to facilitate insertion of the screw assembly into a predefined cavity within a patient's bone. Relative to the expanded configuration, the collapsed configuration of the screw assembly may have a lower profile, e.g., a smaller outer diameter. For example, in the collapsed configuration, the assembly may be substantially cylindrically shaped, with each of the blades extending parallel to and in close contact with an outer surface of the support anchor. However, it will be appreciated that the assembly may generally be the same shape as a bore or cavity into which it is to be implanted.

FIG. 5 illustrates the pedicle screw assembly 400 in the expanded configuration. In this configuration, the one or more blades 404 are attached, welded, or otherwise coupled at the base such that they are configured to bias axially away from a longitudinal axis of the retractable screw 406 and/or the cannulated support anchor 402. In some embodiments, the screw assembly 100 is configured to transition between the collapsed (FIG. 4) and expanded (FIG. 5) configurations upon movement of the retractable screw 406 or a similarly structured shaft within cannula or channel 403 of support anchor 402, e.g., by inserting the retractable screw 406 within cannula 403 towards the distal end. In particular, the distal-facing abutment surface and/or abutment edge of the screw head portion 406*a* may contact the inner-facing surface 404*a* of one or more of the blades. For example, as the screw is inserted, or otherwise travels proximally to distally within the support anchor, the abutment surface of the shaft head portion may slide along the threaded inner surface 404*a* of the blades 404, thus pushing the blades outwardly until the screw assembly reaches a desired outer diameter. To this end, each of the blades may be configured to selectively engage with the retractable shaft head portion at distinct positions along the travel path of the retractable shaft. For example, a first blade or first pair of blades may be configured to engage with the retractable shaft and begin to expand at first position along the travel path of the retractable shaft, and a second blade or second pair of blades may be configured to engage with the retractable shaft and begin to expand at a second position farther down (i.e., more distally) the travel path of the retractable shaft. To this end, the surgeon may be able to decide how many blades to deploy or expand based on how far the retractable shaft is inserted. If the surgeon decides that the bone surrounding pedicle walls are too weak, then only the first blade or pair of blades can be selectively deployed or expanded.

In various aspects, an amount of biasing of the blades may vary from the proximal end of the assembly to the distal end of the assembly. In some embodiments, the amount of biasing is greatest along the distal end and the least along the proximal end. In some embodiments, in the expanded configuration, the blades may be biased away from the support anchor at an acute angle, effectively creating a right triangle between the blade and the support anchor. The acute angle may be in a range of, e.g., about 10 degrees to about 30 degrees, and preferably about 20 degrees. In other embodiments, in the expanded configuration, the blades may curve away from the support anchor, such as when the base portion of the blades are fixed to the support anchor. By way of non-limiting example, a maximum distance between the distal tip of the blade and an outer surface of the support anchor, along an axis perpendicular to the longitudinal axis of the support anchor, may be in a range of about 2 to 20 mm, and preferably around 9 mm. In this way, distal ends of the blades are the farthest away from the support anchor and can provide maximal bone purchase along the distal portion of the screw assembly. This may be particularly advantageous where the screw assembly is implanted such that the distal end of the screw assembly is implanted in cancellous bone, which may be subject to bone loss and require additional purchase to prevent movement and/or screw pull-out. It will be appreciated that the amount of biasing may vary depending on the intended implantation site.

FIG. 3 shows a cross section of the pedicle screw assembly 100. As shown, cannulated support anchor 102 comprises a plurality of slots or grooves 105 along an outer surface of the support anchor 102 that are shaped and dimensioned for the blades to sit in. As the retractable screw 106 is retracted, portions of the blades 104 with move outward from within the slots 105.

In various aspects, an amount of biasing of the blades may vary from the proximal end of the assembly to the distal end of the assembly. In some embodiments, the amount of biasing is greatest along the distal end and the least along the proximal end. In some embodiments, in the expanded configuration, the blades may be biased away from the support anchor at an acute angle, effectively creating a right triangle between the blade and the support anchor. The acute angle may be in a range of, e.g., about 10 degrees to about 30 degrees, and preferably about 20 degrees. In other embodiments, in the expanded configuration, the blades may curve away from the support anchor, such as when the base portion of the blades are fixed to the support anchor. By way of non-limiting example, a maximum distance between the distal tip of the blade and an outer surface of the support anchor, along an axis perpendicular to the longitudinal axis of the support anchor, may be in a range of about 2 to 20 mm, and preferably around 9 mm. In this way, distal ends of the blades are the farthest away from the support anchor and can provide maximal bone purchase along the distal portion of the screw assembly. This may be particularly advantageous where the screw assembly is implanted such that the distal end of the screw assembly is implanted in cancellous bone, which may be subject to bone loss and require additional purchase to prevent movement and/or screw pull-out. It will be appreciated that the amount of biasing may vary depending on the intended implantation site.

Dimensions of the screw assembly may vary depending on the anatomy and position in which it will be implanted. For example, a length of the pedicle screw may be in a range of about 10 mm to 50 mm, for example about 25-30 mm. For example, a length of the retractable shaft may be in a range of about 10 mm to 35 mm, for example about 25-30 mm. A length of the one or more blades may be in a range of about 30 to 60 mm. Where the blade is spear-shaped, a length of the head of the spear may be in a range of about 5 to 25 mm and a length of the shaft of the spear may be in a range of about 15 to 35 mm. A diameter of the screw assembly in the expanded configuration may be in a range of about 2 to 10 mm. A diameter of the screw assembly in the collapsed configuration may be in a range of about 1 to 8 mm.

It will be appreciated that any of the screw assembly components described herein may have one or more surface features to assist with implantation, bone purchase, and/or osteointegration. For example, any of the components described herein may have a textured or roughened outer surface that may be, for example, threads, cylindrical ribs, nubs or bumps, and the like.

Similarly, any of the screw assembly components described herein may be composed of one or more materials to assist with implantation, bone purchase, biocompatibility, and/or osteointegration. By way of non-limiting example, the screw assembly may comprise bio-compatible material (s), for example, allograft, allograft bone; polyetheretherketones (PEEK), high molecular weight polyethylene (HMWPE), carbon fiber, and/or any other synthetic material that can be manufactured and implanted into the body, etc. Some components, e.g., the screw and the blades, may be comprised of a metal, which may be flexible. It will be appreciated that each of the components may be composed of the same or different materials.

Figure 6:
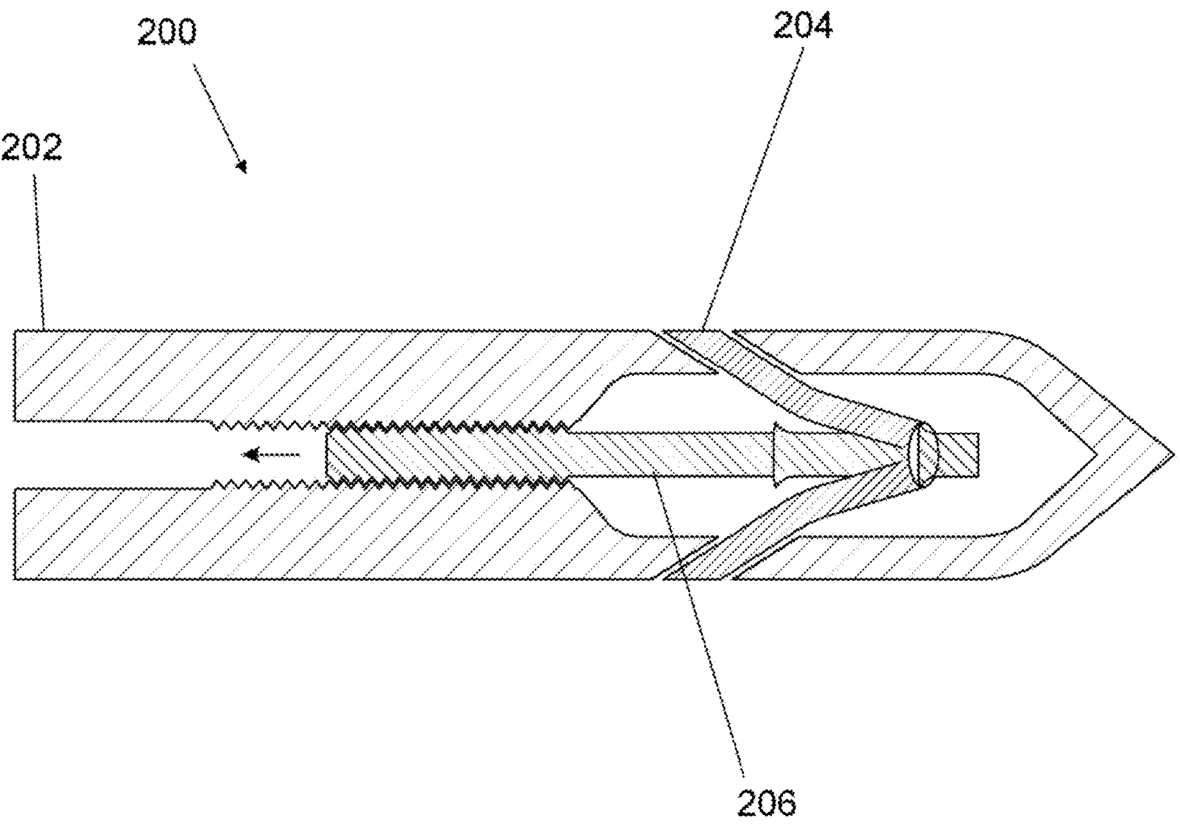
FIG. 6 is a side, cross-sectional view of another example embodiment of a pedicle screw assembly in the collapsed configuration in accordance with the present disclosure.

FIG. 6 illustrates another alternative embodiment of a pedicle screw assembly 200 in accordance with the present invention. Like the embodiments of FIGS. 1-5, this pedicle screw assembly 200 comprises a cannulated support anchor 202 including movable portions in the form of multiple blades 204 for assisting with bone purchase, and a retractable shaft 206 configured for insertion therein. The one or more blades may be operatively connected to the screw head, such that lateral movement (e.g., retraction) of the screw within the shaft moves the blades between a collapsed configuration and an expanded configuration. In this embodiment, the one or more blades are disposed at least partially within the support anchor. In the collapsed configuration, the blades may be disposed entirely within the support anchor. In the expanded configuration, at least a portion of the blades may extend through a corresponding aperture in the support anchor and into adjacent bone tissue. While the blades in the illustrated embodiment are disposed along a distal end of the assembly, it will be appreciated that the location of the blades along the proximal/distal axis of the assembly may vary to accommodate a particular anatomy. Furthermore, the number of blades may vary depending on the amount of purchase necessary and the size of the implantation site.

Screw Assembly Device and System Operation and Methods for Using Same

Also disclosed herein are methods of making and using the disclosed screw assemblies, devices, apparatuses, and systems. For example, in another exemplary aspect, the present disclosure provides a method for implanting a disclosed pedicle screw assembly. In further aspects, the pedicle screw assembly may be implanted in bone tissue.

Figure 7:
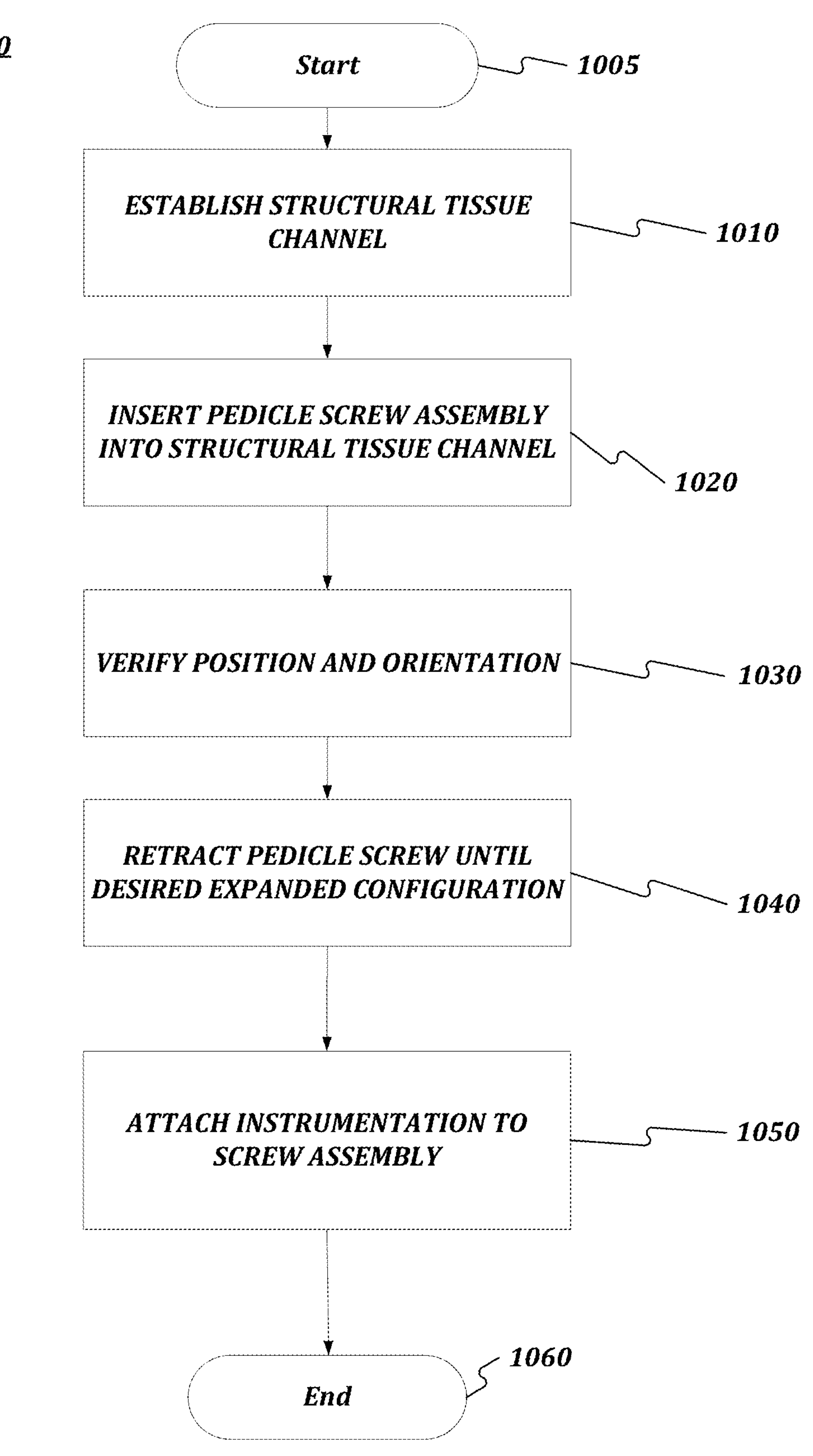
FIG. 7 is a flowchart illustrating an example surgical method using the disclosed pedicle screw assemblies in accordance with the present disclosure.

FIG. 7 is a flow chart is depiction setting forth various stages involved in a method 1000 consistent with an embodiment of the disclosure for using the disclosed screw assemblies, devices, and systems. Method 1000 may be implemented using, at least in part, for example, device 100, 200, or 400, as described in more detail with respect to FIGS. 1-6.

Device 100 may comprise support anchor 102 and retractable shaft 106 for operating the device components, for example, for moving blades 104 radially outwardly from a collapsed configuration to an expanded configuration upon retraction of the retractable shaft within the support anchor. Furthermore, although stages are disclosed with reference to device 100, it should be understood that other disclosed device embodiments may enable the operation of method 1000, including, but not limited to, other device mechanisms, mechanical components, tissue properties (e.g., bone type, etc.), patient conditions, and the like. Further still, although the stages illustrated by the flow charts are disclosed in a particular order, it should be understood that the order is disclosed for illustrative purposes only. Stages may be combined, separated, reordered, and various intermediary stages may exist. Accordingly, it should be understood that the various stages illustrated within the flow chart may be, in various embodiments, performed in arrangements that differ from the ones illustrated. Moreover, various stages may be added or removed from the flow charts without altering or deterring from the fundamental scope of the depicted methods and systems disclosed herein. It will be appreciated that pedicle screw assemblies as presented herein may be useful in a variety of surgical procedures, e.g., spinal reconstruction surgery, spinal fusion, spinal reworking surgery, and the like. One advantage of the present invention is that it may be suitable for use with existing surgical techniques requiring pedicle screws. In relevant part, implanting pedicle screw assemblies according to the present disclosure may involve a surgeon creating a channel in a patient's bone, e.g., within a pedicle and/or an associated vertebral body. A next step may involve the surgeon inserting the entire screw assembly, in the collapsed configuration, into the channel. Once properly positioned in the desired location, the surgeon may then retract the retractable shaft within the support channel, e.g., by inserting a screwdriver into the support channel and turning the screw such that the screw threads engage the inner threads of the support channel. Retracting the screw within the support channel may cause one or more blades of the screw assembly to bias outwardly. In some embodiments, the biasing begins along the distal end of the assembly and continues proximally as the screw is retracted. The surgeon may continue to retract the screw until the desired amount of blade biasing has been achieved.

Method 1000 may begin at starting block 1005 and proceed to stage 1010, where a passage or channel is established or formed in a portion of structural tissue. A structural tissue channel may be established by any method currently or prospectively utilized, for example, using a gear shift, drill and a drill bit or a pick styled device. However, one skilled in the art would recognize that the method of establishing a structural tissue channel may vary according to many factors such as the type of structural tissue, the location of the desired structural tissue channel, or other factors specific to the variance associated with different patients' anatomy or specific needs and surgeon's preference.

From stage 1010, where the passage or channel is established or formed, method 1000 may proceed to stage 1020 where a pedicle screw assembly in the collapsed configuration may be inserted into the established structural tissue channel. The pedicle screw assembly may be characterized by, but not limited to, the various embodiments depicted above in FIGS. 1-4 and/or may include expandable characteristics with one or more means of holding and orienting the support anchor. One skilled in the art would recognize that the insertion of the pedicle screw assembly and support anchor may vary according to factors specific to the variance associated with different patients' anatomy or specific types of structural tissue or needs as required to successfully complete the task.

From stage 1020, where the pedicle screw assembly in the collapsed configuration is inserted, method 1000 may proceed to stage 1030, where proper positioning and orientation may be verified using, for example, visual cues and/or markers and radiographs. For example, markers may provide useful information regarding the position of the pedicle screw assembly in the channel or pedicle including, but not limited to, the position of the support anchor in the channel or pedicle, the length and width of the pedicle screw assembly once inside the channel or pedicle, the angle of entry into the channel or pedicle, and/or the depth of the pedicle screw assembly in the channel or pedicle.

From stage 1030, where the proper positioning and orientation may be verified, method 1000 may proceed to stage 1040, where the retractable shaft may be retracted within into the support structure, for example, by turning the screw until the desired expanded configuration is achieved.

From stage 1040, where the retractable shaft may be retracted to achieve the desired expanded configuration of the screw assembly, method 1000 may proceed to stage 1050, where, if needed, any number of items may be attached or otherwise. For example, a plate, rods, or hooks. After stage 1050, method 1000 may end at stage 1060.

Also disclosed herein are kits comprising the disclosed screw assemblies and devices. For example, in an exemplary aspect, the present disclosure provides a pedicle screw kit comprising: a disclosed screw assembly or device; and instructions for using the device in connection with a medical procedure. In further aspects, the instruction and/or method may comprise any surgical method and/or method step. In still further aspects, the method and/or method step may comprise affixing or implanting a disclosed screw assembly or device to a patient, such as a human or mammal.

In further aspects, the present invention includes at least the following aspects: Aspect 1: A pedicle screw assembly, comprising: a support anchor having one or more blades and a channel with a threaded inner surface configured to mate with a threaded shaft; and a retractable shaft having a distal head portion and a proximal threaded shaft body; and wherein the one or more blades are operatively connected to the retractable shaft, such that the blades are biased radially outwardly from a collapsed configuration to an expanded configuration upon lateral movement of the retractable shaft within the support anchor.

Aspect 2: The screw assembly of Aspect 1, wherein the distal head portion of the retractable shaft comprises a proximal abutment edge.

Aspect 3: The screw assembly of Aspect 2, wherein the distal head portion of the retractable shaft comprises a spear having a distal point and a proximal abutment edge.

Aspect 4: The screw assembly of Aspect 3, wherein the proximal abutment edge of the distal head portion is configured to push the one or more blades radially outward as the retractable shaft retracts within the support anchor.

Aspect 5: The screw assembly of Aspect 4, wherein at least one of the one or more blades has a sloped inner surface terminating in a sharp point along a distal end thereof, the sloped inner surface being configured to abut the proximal abutment edge of the distal head portion as the retractable shaft travels within the support anchor.

Aspect 6: The screw assembly of Aspect 1, wherein biasing of the blades begins along a distal portion of the screw assembly upon retraction of the retractable shaft within the support anchor.

Aspect 7: The screw assembly of Aspect 5, wherein the one or more blades are configured to bias to varying degrees along an entire length of the screw assembly in the expanded configuration.

Aspect 8: The screw assembly of Aspect 1, wherein the one or more blades comprises two blades disposed on opposing outer surfaces of the support anchor.

Aspect 9: The screw assembly of Aspect 1, wherein the one or more blades comprises four blades, each of the four blades being disposed opposite to another along an outer surface of the support anchor.

Aspect 10: The screw assembly of Aspect 8, wherein at least one of the one or more blades has a plurality of pointed projections extending radially therefrom.

Aspect 11: The screw assembly of Aspect 1, wherein the screw assembly is substantially cylindrical when in the contracted configuration.

Aspect 12: The screw assembly of Aspect 2, wherein the distal head portion of the retractable shaft comprises a distal abutment edge.

Aspect 13: The screw assembly of Aspect 12, wherein the distal abutment edge of the distal head portion is configured to push the one or more blades radially outward as the retractable shaft travels proximal to distal within the support anchor.

Aspect 14: The screw assembly of Aspect 13, wherein at least one of the one or more blades has a sloped inner surface terminating in a sharp point along a distal end thereof, the sloped inner surface being configured to abut the distal abutment edge of the distal head portion as the retractable shaft travels proximal to distal within the support anchor.

Aspect 15: The screw assembly of Aspect 14, wherein biasing of the blades begins along a distal portion of the screw assembly upon retraction of the retractable shaft within the support anchor.

Aspect 16: The screw assembly of Aspect 5, wherein the one or more blades are configured to bias to varying degrees along an entire length of the screw assembly in the expanded configuration.

Aspect 17: The screw assembly of Aspect 3, wherein at least one of the one or more blades has a sloped inner surface terminating in a sharp point along a distal end thereof, the sloped inner surface being configured to abut the proximal abutment edge of the spear as the spear slides within the support anchor.

Aspect 18: The screw assembly of any preceding aspect, further comprising a plurality of blades.

Aspect 19: The screw assembly of any preceding aspect, wherein each of the blades are configured to selectively engage with the retractable shaft at various positions along a travel path of the retractable shaft.

Aspect 20: The screw assembly of any preceding aspect, wherein a first blade or first pair of blades are configured to engage with the retractable shaft and begin to expand at first position along a travel path of the retractable shaft, Aspect 21: The screw assembly of aspect 20, wherein a second blade or second pair of blades may be configured to engage with the retractable shaft and begin to expand at a second position along the travel path of the retractable shaft.

Aspect 22: The screw assembly of any preceding aspect, wherein a first grouping of blades are configured to engage with the retractable shaft and begin to expand at first position along a travel path of the retractable shaft, Aspect 23: The screw assembly of aspect 22, wherein a second grouping of blades may be configured to engage with the retractable shaft and begin to expand at a second position along the travel path of the retractable shaft.

Aspect 24: The screw assembly of any preceding aspect, wherein the plurality of blades comprises at least one non-expandable blade.

Aspect 25: The screw assembly of any preceding aspect, wherein the plurality of blades comprises a plurality of non-expandable blades.

Aspect 26: A pedicle screw assembly, comprising: a retractable shaft having a distal head portion and a proximal threaded shaft; a support anchor having a proximal, threaded inner surface that is configured to mate with the threaded shaft of the retractable shaft and a distal, open cavity for housing the distal head portion of the retractable shaft therein; and one or more blades operatively connected to the distal head portion of the retractable shaft, such that the blades expand radially outwardly through apertures in the support anchor upon lateral movement of the retractable shaft within the support anchor.

Aspect 27: The screw assembly of any preceding aspect, wherein the one or more blades comprises two blades disposed on opposing outer surfaces of the support anchor.

Aspect 28: The screw assembly of any preceding aspect, wherein the one or more blades comprises four blades, each of the four blades being disposed opposite to another along an outer surface of the support anchor.

Aspect 29: A method of implanting a pedicle screw assembly inside a patient, comprising: forming a channel in a patient's treatment location; inserting the screw assembly into the channel in a collapsed configuration, the screw assembly comprising a retractable shaft, a support anchor, and one or more blades; and proximally retracting the screw within the support anchor to bias one or more blades into an expanded configuration in which the one or more blades extend axially away from the screw assembly.

Aspect 30: The method of Aspect 29, wherein retracting the screw comprises rotating the screw within the support anchor, such that threads of the screw engage inner threads of the support anchor.

Aspect 31: The method of Aspect 29, wherein the biasing of the blades begins along a distal portion of the screw assembly.

Aspect 32: The method of Aspect 29, wherein the biasing of the blades involves biasing the blades along an entire longitudinal length of the screw assembly.

Both the foregoing overview and the following detailed description provide examples and are explanatory only. Accordingly, the foregoing overview and the following detailed description should not be considered to be restrictive. Further, features or variations may be provided in addition to those set forth herein. For example, embodiments may be directed to various feature combinations and sub-combinations described in the detailed description.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A pedicle screw assembly, comprising:

a support anchor having one or more blades and a channel with a threaded inner surface, wherein the support anchor includes one or more grooves formed in an outer surface thereof, and wherein each of the one or more blades is positioned within a corresponding groove; and a retractable shaft having a distal head portion and a proximal threaded shaft body configured to mate with the threaded inner surface; and wherein the one or more blades are operatively connected to the retractable shaft, such that the one or more blades are biased radially outwardly from a collapsed configuration to an expanded configuration upon lateral movement of the retractable shaft within the support anchor, wherein, in the expanded configuration, each of the one or more blades extends radially outward from its corresponding groove to project beyond the outer surface of the support anchor.

2. The pedicle screw assembly of claim 1, wherein the distal head portion of the retractable shaft comprises a proximal abutment edge.

3. The pedicle screw assembly of claim 2, wherein the distal head portion of the retractable shaft comprises a spear having a distal point and the proximal abutment edge.

4. The pedicle screw assembly of claim 3, wherein the proximal abutment edge of the distal head portion is configured to push the one or more blades radially outward as the retractable shaft retracts within the support anchor.

5. The pedicle screw assembly of claim 4, wherein at least one of the one or more blades has a sloped inner surface terminating in a sharp point along a distal end thereof, the sloped inner surface being configured to abut the proximal abutment edge of the distal head portion as the retractable shaft travels within the support anchor.

6. The pedicle screw assembly of claim 2, wherein biasing of the one or more blades begins along a distal portion of the pedicle screw assembly upon retraction of the retractable shaft within the support anchor.

7. The pedicle screw assembly of claim 6, wherein the one or more blades are configured such that an amount of biasing of the one or more blades varies from a proximal end of the pedicle screw assembly to a distal end of the pedicle screw assembly.

8. The pedicle screw assembly of claim 7, wherein the one or more blades comprises four blades, each of the four blades being disposed opposite to another along an outer surface of the support anchor.

9. The pedicle screw assembly of claim 8, wherein each of the one or more blades is positioned within a corresponding groove formed in the outer surface of the support anchor.

10. The pedicle screw assembly of claim 8, wherein the pedicle screw assembly is substantially cylindrical when in the collapsed configuration.

11. The pedicle screw assembly of claim 2, wherein the distal head portion of the retractable shaft comprises a distal abutment edge; and wherein the distal abutment edge of the distal head portion is configured to push the one or more blades radially outward as the retractable shaft travels proximal to distal within the support anchor.

12. The pedicle screw assembly of claim 11, wherein at least one of the one or more blades has a sloped inner surface terminating in a sharp point along a distal end thereof, the sloped inner surface being configured to abut the distal abutment edge of the distal head portion as the retractable shaft travels proximal to distal within the support anchor.

13. The pedicle screw assembly of claim 12, wherein biasing of the one or more blades begins along a distal portion of the pedicle screw assembly upon insertion of the retractable shaft within the support anchor.

14. The pedicle screw assembly of claim 7, wherein the one or more blades comprises a first blade or first pair of blades configured to engage with the retractable shaft and begin to expand at a first position along a travel path of the retractable shaft; and wherein the one or more blades further comprises a second blade or second pair of blades configured to engage with the retractable shaft and begin to expand at a second position along the travel path of the retractable shaft.

15. The pedicle screw assembly of claim 1, the support anchor further comprises a non-expandable blade.

16. A method of implanting the pedicle screw assembly of claim 1 inside a patient, comprising:

forming a channel in a patient treatment location;

inserting the pedicle screw assembly into the channel in the collapsed configuration; and proximally retracting the retractable shaft within the support anchor to bias the one or more blades into the expanded configuration in which the one or more blades extend axially away from the pedicle screw assembly.

17. The method of claim 16, wherein retracting comprises rotating the retractable shaft within the support anchor, such threads of the retractable shaft engage inner threads of the support anchor.

* * * * *